(12) United States Patent
Hsieh et al.

(10) Patent No.: US 11,871,775 B2
(45) Date of Patent: Jan. 16, 2024

(54) METHOD OF INHIBITING ORAL PATHOGENS

(71) Applicant: GLAC BIOTECH CO., LTD., Tainan (TW)

(72) Inventors: Pei-Shan Hsieh, Tainan (TW);
Chung-Wei Kuo, Tainan (TW);
Yi-Chun Tsai, Tainan (TW);
Hsieh-Hsun Ho, Tainan (TW); Yi-Wei Kuo, Tainan (TW)

(73) Assignee: GLAC BIOTECH CO., LTD., Tainan (TW)

( * ) Notice: Subject to any disclaimer, the term of this patent is extended or adjusted under 35 U.S.C. 154(b) by 397 days.

(21) Appl. No.: 16/685,445

(22) Filed: Nov. 15, 2019

(65) Prior Publication Data

US 2020/0100536 A1    Apr. 2, 2020

Related U.S. Application Data

(63) Continuation of application No. 15/867,301, filed on Jan. 10, 2018, now abandoned.

(30) Foreign Application Priority Data

Jan. 24, 2017 (TW) .................. 106102613

(51) Int. Cl.
| | | |
|---|---|---|
| *A23L 33/135* | (2016.01) | |
| *A61Q 11/00* | (2006.01) | |
| *A61K 35/747* | (2015.01) | |
| *A61P 1/02* | (2006.01) | |
| *A61K 8/99* | (2017.01) | |
| *A61K 45/06* | (2006.01) | |
| *A61Q 17/00* | (2006.01) | |

(52) U.S. Cl.
CPC .............. *A23L 33/135* (2016.08); *A61K 8/99* (2013.01); *A61K 35/747* (2013.01); *A61K 45/06* (2013.01); *A61P 1/02* (2018.01); *A61Q 11/00* (2013.01); *A61Q 17/005* (2013.01); *A23V 2002/00* (2013.01)

(58) Field of Classification Search
CPC .......... A61K 45/06; A23L 33/135; A61P 1/02
See application file for complete search history.

(56) References Cited

PUBLICATIONS

Simark-Mattsson et al., Eur J Oral Sci., 2007, 115:308-314.*
Liu et al, "Research and application of oral probiotics in the prevention and treatment of oral diseases," Journal of Pharmaceutical Research, 2015, vol. 34, No. 6, pp. 357-360, 4 pages.

* cited by examiner

*Primary Examiner* — Vera Afremova
(74) *Attorney, Agent, or Firm* — Muncy, Geissler, Olds & Lowe, P.C.

(57) ABSTRACT

A method of inhibiting oral pathogens comprising administering to a subject in need thereof an effective amount of *Lactobacillus* strain-containing food composite, medical composite and oral cleaning composite. The food composite, medical composite and oral cleaning composite comprises at least one *Lactobacillus* strain, which is at least one isolated *Lactobacillus* strain selected from a group including *Lactobacillus acidophilus* F-1 strain, CCTCC NO: M2011124; *Lactobacillus salivarius* subsp. *salicinius* AP-32 strain, CCTCC NO: M2011127; *Lactobacillus reuteri* GL-104 strain, CCTCC NO: M209138; *Lactobacillus paracasei* GL-156 strain, CCTCC NO: M2014590; *Lactobacillus helveticus* RE-78 strain, CGMCC No. 13513; *Lactobacillus rhamnosus* CT-53 strain, CCTCC NO: M2011129; and *Lactobacillus paracasei* ET-66 strain, CGMCC No. 13514, which are respectively preserved in China Center for Type Culture Collection (CCTCC) and China General Microbiological Culture Collection Center (CGMCC).

14 Claims, 5 Drawing Sheets

METHOD OF INHIBITING ORAL PATHOGENS

CROSS REFERENCE TO RELATED APPLICATION

This application is a continuation of U.S. patent application Ser. No. 15/867,301, filed Jan. 10, 2018, which claimed priority to Taiwan Patent application Ser. No. 106102613, filed Jan. 24, 2017, which is hereby incorporated by reference in its entirety.

BACKGROUND OF THE INVENTION

1. Field of the Invention

The present invention relates to a method of inhibiting oral pathogens, comprises administering food composite, an oral cleaning composite and a medical composite, particularly to a food composite, an oral cleaning composite and a medical composite, which carry *Lactobacillus* strains able to inhibit oral pathogens.

2. Description of the Prior Art

The healthcare of milk teeth of children would influence the future growth of permanent teeth. It is very important to clean the oral cavity from the infancy. The bacteria growing in the oral cavity are likely to adhere to the surface of the gingiva. After the milk teeth grow up, the bacteria will direct adhere to the milk teeth of children and cause dental caries. Milk teeth are the basis of permanent teeth, sustaining appropriate space for the growth of permanent teeth. If the parents do not nurse the milk teeth of the child well but allow caries to occur, caries will cause the space to lose. Further, bacteria and pustules will appear in the permanent teeth growing later, not only making the permanent teeth likely to decay but also increasing the incidence rate of periodontitis in maturity and senility.

Since 1991, Taiwan government has invested a lot of money in moving the free children teeth fluoridizing policy. The policy decreases the prevalence rate of caries by 15% and decreases two decayed teeth for each child in average. However, the caries protection rate of Taiwan ranks rearwards among Asian nations (the second from the last). WHO expected that 95% under-five children are completely free of caries and that the 12-year-old children have less than two decayed teeth in average for all the member nations in 2010. At present, 20% Taiwanese children are free of carries, and the 12-year-old children have more than three decayed teeth in average, which is far below the target of WHO. Therefore, we should pay more attention to the prevention of caries.

In general, *Lactobacillus* (LAB) is regarded as only helpful to the health of intestines. There are tens of thousands of *Lactobacillus* strains existing in the nature. However, only few of them have the potential of protecting oral health and whitening teeth. The ability of inhibiting oral pathogens, the ability of adhering to the epithelial cells of oral mucosa, the ability of inhibiting pathogens and generating hydrogen peroxide while a *Lactobacillus* strain exists in teeth cleaning products, etc. determine whether the *Lactobacillus* strain can function in the oral cavity to control the balance of the microecological system in the oral cavity, and thus are the factors to screen the *Lactobacillus* strains helpful to health of oral cavities and whitening of teeth.

Documents point out that probiotics compete with pathogens for the living area they attach to and the nutrition they feed on. Thus, pathogens are driven to aggregate. The probiotics also secrete bacteria-inhibiting material, which can weaken pathogens or even kill pathogens. Thus, the oral pathogens are decreased, and health of oral cavities is kept. Furthermore, the probiotics also secrete hydrogen peroxide, which can eliminate oral odor and whiten teeth.

So far, only few *Lactobacillus* strains have been proved to be effective in maintaining oral cavity health and whitening teeth. It is not the species of *Lactobacillus* but the strains of *Lactobacillus* that can provide the special health-enhancing functions for human bodies. The *Lactobacillus* strain providing special health-enhancing functions is called the functional probiotics. (Refer to Guidelines for the evaluation of probiotics in food; Report of joint FAO/WHO working group on drafting guidelines for the evaluation of probiotics in food; London Ontario, Canada April 30 and May 1, 2002: 1-7.)

Accordingly, the related manufacturers and organizations are eager to develop functional probiotics able to inhibit oral pathogens.

SUMMARY OF THE INVENTION

The present invention provides a method of inhibiting oral pathogens, comprises administering food composite, an oral cleaning composite and a medical composite, which carry *Lactobacillus* strains, and which can inhibit growth of oral pathogens and maintain health of oral cavities.

In one embodiment, the *Lactobacillus* strain-containing food composite of the present invention comprises at least one *Lactobacillus* strain able to inhibit oral pathogens; and an excipient or diluent, which is physiologically acceptable. The *Lactobacillus* strain is at least one isolated *Lactobacillus* strain selected from a group including *Lactobacillus acidophilus* F-1 strain, CCTCC NO: M2011124; *Lactobacillus salivarius* subsp. *salicinius* AP-32 strain, CCTCC NO: M2011127; *Lactobacillus reuteri* GL-104 strain, CCTCC NO: M209138; *Lactobacillus paracasei* GL-156 strain, CCTCC NO: M2014590; *Lactobacillus helveticus* RE-78 strain, CGMCC No. 13513; *Lactobacillus rhamnosus* CT-53 strain, CCTCC NO: M2011129; and *Lactobacillus paracasei* ET-66 strain, CGMCC No. 13514. The abovementioned strains are respectively preserved in China Center for Type Culture Collection (abbreviated as CCTCC) and China General Microbiological Culture Collection Center (abbreviated as CGMCC).

In another embodiment, the *Lactobacillus* strain-containing medical composite of the present invention comprises at least one *Lactobacillus* strain able to inhibit oral pathogens; and an excipient or diluent, which is medically acceptable. The *Lactobacillus* strain is at least one isolated *Lactobacillus* strain selected from a group including *Lactobacillus acidophilus* F-1 strain, CCTCC NO: M2011124; *Lactobacillus salivarius* subsp. *salicinius* AP-32 strain, CCTCC NO: M2011127; *Lactobacillus reuteri* GL-104 strain, CCTCC NO: M209138; *Lactobacillus paracasei* GL-156 strain, CCTCC NO: M2014590; *Lactobacillus helveticus* RE-78 strain, CGMCC No. 13513; *Lactobacillus rhamnosus* CT-53 strain, CCTCC NO: M2011129; and *Lactobacillus paracasei* ET-66 strain, CGMCC No. 13514. The abovementioned strains are respectively preserved in CCTCC and CGMCC.

In yet another embodiment, the *Lactobacillus* strain-containing oral cleaning composite of the present invention comprises at least one active *Lactobacillus* strain able to inhibit oral pathogens; and an excipient or diluent, which is physiologically acceptable. The *Lactobacillus* strain is at least one isolated *Lactobacillus* strain selected from a group including *Lactobacillus acidophilus* F-1 strain, CCTCC NO: M2011124; *Lactobacillus salivarius* subsp. *salicinius* AP-32 strain, CCTCC NO: M2011127; *Lactobacillus reuteri* GL-104 strain, CCTCC NO: M209138; *Lactobacillus paracasei* GL-156 strain, CCTCC NO: M2014590; *Lactobacillus helveticus* RE-78 strain, CGMCC No. 13513; *Lactobacillus rhamnosus* CT-53 strain, CCTCC NO: M2011129; and *Lactobacillus paracasei* ET-66 strain, CGMCC No. 13514. The abovementioned strains are respectively preserved in CCTCC and CGMCC.

Below, embodiments are described in detail in cooperation with the attached drawings to make easily understood the objectives, technical contents, characteristics and accomplishments of the present invention.

BRIEF DESCRIPTION OF THE DRAWINGS

The patent or application file contains at least one drawing executed in color. Copies of this patent application publication with color drawing(s) will be provided by the Office upon request and payment of the necessary fee.

The foregoing conceptions and their accompanying advantages of this invention will become more readily appreciated after being better understood by referring to the following detailed description, in conjunction with the accompanying drawings, wherein.

DESCRIPTION OF THE PREFERRED EMBODIMENTS

The present invention will be described in detail with embodiments and attached drawings below. However, these embodiments are only to exemplify the present invention but not to limit the scope of the present invention. In addition to the embodiments described in the specification, the present invention also applies to other embodiments. Further, any modification, variation, or substitution, which can be easily made by the persons skilled in that art according to the embodiment of the present invention, is to be also included within the scope of the present invention, which is based on the claims stated below. Although many special details are provided herein to make the readers more fully understand the present invention, the present invention can still be practiced under a condition that these special details are partially or completely omitted. Besides, the elements or steps, which are well known by the persons skilled in the art, are not described herein lest the present invention be limited unnecessarily. Similar or identical elements are denoted with similar or identical symbols in the drawings. It should be noted: the drawings are only to depict the present invention schematically but not to show the real dimensions or quantities of the present invention. Besides, matterless details are not necessarily depicted in the drawings to achieve conciseness of the drawings.

The freeze-dried cultures of the *Lactobacillus* strains mentioned in the specification have been respectively preserved in CCTCC and CGMCC.

Table. 1 shows the detailed data of the preserved *Lactobacillus* strains.

TABLE.1 data of preserved *lactobacillus* strains

| Strain | Classification | Preservation Code | Preservation Date |
|---|---|---|---|
| F-1 | *Lactobacillus acidophilus* | CCTCC NO: M2011124 | Apr. 10, 2011 |
| AP-32 | *Lactobacillus salivarius* subsp. *salicinius* | CCTCC NO: M2011127 | Apr. 10, 2011 |
| GL-104 | *Lactobacillus reuteri* | CCTCC NO: M209138 | Aug. 7, 2009 |
| GL-156 | *Lactobacillus paracasei* | CCTCC NO: M2014590 | Nov. 24, 2014 |
| RE-78 | *Lactobacillus helveticus* | CGMCC No. 13513 | Dec. 29, 2016 |
| CT-53 | *Lactobacillus rhamnosus* | CCTCC NO: M2011129 | Apr. 10, 2011 |
| ET-66 | *Lactobacillus paracasei* | CGMCC No. 13514 | Dec. 29, 2016 |

The seven preserved *Lactobacillus* strains listed in Table. 1: *Lactobacillus acidophilus* F-1 strain; *Lactobacillus salivarius* subsp. *salicinius* AP-32 strain; *Lactobacillus reuteri* GL-104 strain; *Lactobacillus paracasei* GL-156 strain; *Lactobacillus helveticus* RE-78 strain; *Lactobacillus rhamnosus* CT-53 strain; and *Lactobacillus paracasei* ET-66 strain are found to have the ability of inhibiting oral pathogens, such as tooth decay bacteria, *Porphyromonas gingivalis*, oral odor bacteria, etc. besides, *Lactobacillus salivarius* subsp. *salicinius* AP-32 strain, *Lactobacillus reuteri* GL-104 strain, *Lactobacillus helveticus* RE-78 strain, and *Lactobacillus rhamnosus* CT-53 strain can secrete hydrogen peroxide, not only inhibiting oral pathogens but also whitening teeth.

Each of the food composite, the oral cleaning composite and the medical composite of the present invention comprises at least one *Lactobacillus* strain able to inhibit oral pathogens. The *Lactobacillus* strain is at least one isolated *Lactobacillus* strain selected from a group including *Lactobacillus acidophilus* F-1 strain, CCTCC NO: M2011124; *Lactobacillus salivarius* subsp. *salicinius* AP-32 strain, CCTCC NO: M2011127; *Lactobacillus reuteri* GL-104 strain, CCTCC NO: M209138; *Lactobacillus paracasei* GL-156 strain, CCTCC NO: M2014590; *Lactobacillus helveticus* RE-78 strain, CGMCC No. 13513; *Lactobacillus rhamnosus* CT-53 strain, CCTCC NO: M2011129; and *Lactobacillus paracasei* ET-66 strain, CGMCC No. 13514. The abovementioned strains are respectively preserved in CCTCC and CGMCC. Each of the food composite and the oral cleaning composite further comprises a physiologically-acceptable excipient, a physiologically-acceptable diluent, or a physiologically-acceptable carrier. The medical composite further comprises a medically-acceptable excipient or a medically-acceptable diluent. The *Lactobacillus* strain used in the present invention may be an active strain or a deactivated strain.

In the embodiment of a food composite, the physiologically-acceptable excipient or the physiologically-acceptable diluent may be a food. The food may be but is not limited to be a milk-based drink, tea, coffee, a chewing gum, a tooth-cleaning candy (such as an oral strip, a chewable tablet, or, or jelly sweets), dried meat for pets, or a combination thereof. The milk-based drink may include fermented milk, sour milk, cheese, or milk powder. In the embodiment of an oral cleaning composite, the excipient or diluent may be a toothpaste, a dental powder, a mouthwash, a fresh-breath spray, a fluorine-coating agent (such as a fluoridizing agent smeared on the teeth of children), a false tooth cleaning agent, a pet's tooth gel, or a hairball remedy; the carrier may be a toothbrush, an interdental brush, a dental floss, an oral cotton stick, or a pet's dental bone. The medical composite of the present invention may be an oral composite or a topical composite. The oral composite may be in form of a tablet, a capsule, a solution, or a powder.

In the food composite or medical composite of the present invention, the number of the *Lactobacillus* strains is over $10^6$ CFU, more preferably over $10^{10}$ CFU.

It has been known that some strains are effective in inhibiting tooth decay bacteria and *Porphyromonas gingivalis*. Most researches respectively verify the effects of individual strains in oral cavities. The results of these researches show that *Lactobacillus* strains are not always helpful to oral health and that the *Lactobacillus* strains have individual variations in performance (refer to Anna Haukioja, European Journal of Dentistry 2010(4):348-355). Vuotto C, et al. pointed out that probiotics respectively have different abilities in inhibiting pathogens and that even different strains of the same species may have opposite experimental results (refer to International Journal of Oral Science 2014(6): 189-194). These results signify that the strain specificity exists in inhibiting oral pathogens and whitening teeth.

In fact, the experimental results of the present invention show that most *Lactobacillus* strains can neither inhibit oral pathogens nor whiten teeth. The domestic and international documents and reports about the effects of probiotics on oral health have gradually increased recently. In earlier years, it was deemed that the acid generated by various species of lactobacilli favors coexistence of lactobacilli and pathogens, decays odonthyalus of teeth, and leads to caries. However, experimental results show that *Lactobacillus* not only inhibits tooth decay bacteria and *Porphyromonas gingivalis* but also competes with them for living space and nutrition. Thus, oral pathogens are driven to aggregate and easy to remove. However, these features must be confirmed with experiments. Not all strains have identical features and identical experimental results. It should be explained: the strains that the present invention claims only include *Lactobacillus acidophilus* F-1 strain, CCTCC NO: M2011124; *Lactobacillus salivarius* subsp. *salicinius* AP-32 strain, CCTCC NO: M2011127; *Lactobacillus reuteri* GL-104 strain, CCTCC NO: M209138; *Lactobacillus paracasei* GL-156 strain, CCTCC NO: M2014590; *Lactobacillus helveticus* RE-78 strain, CGMCC No. 13513; *Lactobacillus rhamnosus* CT-53 strain, CCTCC NO: M2011129; and *Lactobacillus paracasei* ET-66 strain, CGMCC No. 13514, which are preserved in CCTCC and CGMCC. The claims of the present invention do not include other strains of the abovementioned lactobacilli.

Embodiment I: morphology and general properties of the lactobacilli able to maintain oral health.

Use 16S rDNA sequence analysis and API bacteria identification system to identify the characteristics of the strains in taxonomy. The morphological characteristics and general properties of the abovementioned strains are listed in Table.2:

TABLE 2 morphological characteristics and general properties of *lactobacillus* strains

| Strain | | Morphological characteristics |
|---|---|---|
| *Lactobacillus acidophilus* F-1 | 1. | While cultured in the MRS medium, the body thereof has a short or longer rod-like shape, and two ends of the body are rectangular-shaped. They often appear in single bodies, pairs, or short chains. |
| | 2. | They are gram-positive bacilli, unlikely to generate spores, free of catalase, oxidase and motility, able to grow in aerobic and anaerobic environments, most suitable to grow at a temperature of 37 ± 1° C. They belong to a facultative heterofermentative strains and do not generate gas in glucose metabolism. |
| *Lactobacillus salivarius* subsp. *salicinius* AP-32 | 1. | While cultured in the MRS medium, the body thereof has a short rod-like shape, and two ends of the body are round-shaped. They often appear in single bodies, pairs, or short chains. |
| | 2. | They are gram-positive bacilli, unlikely to generate spores, free of catalase, oxidase and motility, able to grow in aerobic and anaerobic environments, most suitable to grow at a temperature of 37 ± 1° C. They belong to facultative heterofermentative strains and do not generate gas in glucose metabolism. |
| *Lactobacillus reuteri* GL-104 | 1. | While cultured in the MRS medium, the body thereof has a short rod-like shape, and two ends of the body are round-shaped. They often appear in single bodies, pairs, or short chains. |
| | 2. | They are gram-positive bacilli, unlikely to generate spores, free of catalase, oxidase and motility, able to grow in aerobic and anaerobic environments, most suitable to grow at a temperature of 37 ± 1° C. They belong to facultative heterofermentative strains and do not generate gas in glucose metabolism. |
| *Lactobacillus paracasei* GL-156 | 1. | While cultured in the MRS medium, the body thereof has a short rod-like shape, and two ends of the body are round-shaped. They often appear in chains, sometimes in single bodies or pairs. |
| | 2. | They are gram-positive bacilli, unlikely to generate spores, free of catalase, oxidase and motility, able to grow in aerobic and anaerobic environments, most suitable to grow at a temperature of 37 ± 1° C. They belong to facultative heterofermentative strains and do not generate gas in glucose metabolism. |
| *Lactobacillus helveticus* RE-78 | 1. | While cultured in the MRS medium, the body thereof has a short rod-like shape, and two ends of the body are round-shaped. They often appear in single bodies or pairs, sometimes in short chains. |
| | 2. | They are gram-positive bacilli, unlikely to generate spores, free of catalase, oxidase and motility, able to grow in aerobic and anaerobic environments, most suitable to grow at a temperature of 37 ± 1° C. They belong to facultative heterofermentative strains and do not generate gas in glucose metabolism. |
| *Lactobacillus rhamnosus* CT-53 | 1. | While cultured in the MRS medium, the body thereof has a short or longer rod-like shape, and two ends of the body are rectangular-shaped. They often appear in single bodies, pairs, or short chains. |
| | 2. | They are gram-positive bacilli, unlikely to generate spores, free of catalase, oxidase and motility, able to grow in aerobic and anaerobic environments, most suitable to grow at a temperature of 37 ± 1° C. They belong to facultative heterofermentative strains and do not generate gas in glucose metabolism. |
| *Lactobacillus paracasei* | 1. | While cultured in the MRS medium, the body thereof has a short or longer rod-like shape, and |

TABLE 2-continued morphological characteristics and general properties of *lactobacillus* strains

| Strain | Morphological characteristics |
| --- | --- |
| ET-66 | two ends of the body are round-shaped. They often appear in pairs, sometimes in single bodies or short chains.<br>2. They are gram-positive bacilli, unlikely to generate spores, free of catalase, oxidase and motility, able to grow in aerobic and anaerobic environments, most suitable to grow at a temperature of 37 ± 1° C. They belong to facultative heterofermentative strains and do not generate gas in glucose metabolism. |

Embodiment II: analyzing the ability of generating hydrogen peroxide to verify the teeth-whitening function Detect the hydrogen peroxide-generating ability of *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus helveticus* RE-78 strain, *Lactobacillus rhamnosus* CT-53 strain and *Lactobacillus paracasei* ET-66 strain to verify the performance of teeth whitening of the *Lactobacillus* strains of the present invention. The steps of experiments are as follows:
1. prepare a plate for screening the probiotics generating hydrogen peroxide;
2. add 0.25 mg/ml trimethyl borane (TMB) and 0.01 mg/ml horseradish peroxidase (HRP) to the plate;
3. divide the plate into four areas for cultivating strains;
4. after two-day cultivation, blue color appears in the perimeters of the colonies where the *Lactobacillus* strains generating hydrogen peroxide grow;
5. use hydrogen peroxide test paper to detect the concentration hydrogen peroxide in the *Lactobacillus* bodies and the secondary metabolites;
6. centrifugate the liquid of cultivating the lactobacilli at 4500 rpm for 5 minutes;
7. dissolve a portion of *Lactobacillus* bodies in 4.9 ml of 100 mM piperazine-1,4-bisethanesulfonicacid (PIPES) to form a solution;
8. cultivate the solution at a temperature of 37° C. and 220 rpm for 5 hours; centrifugate the cultivated solution; take 10 μL supernatant liquid or the settled bodies; drip the liquid or the bodies to the hydrogen peroxide test paper (Merck) to react for 10 seconds; observe the color variation; compare the color with the colorimetric cards to determine the concentration; record the concentration.

Figure 6:
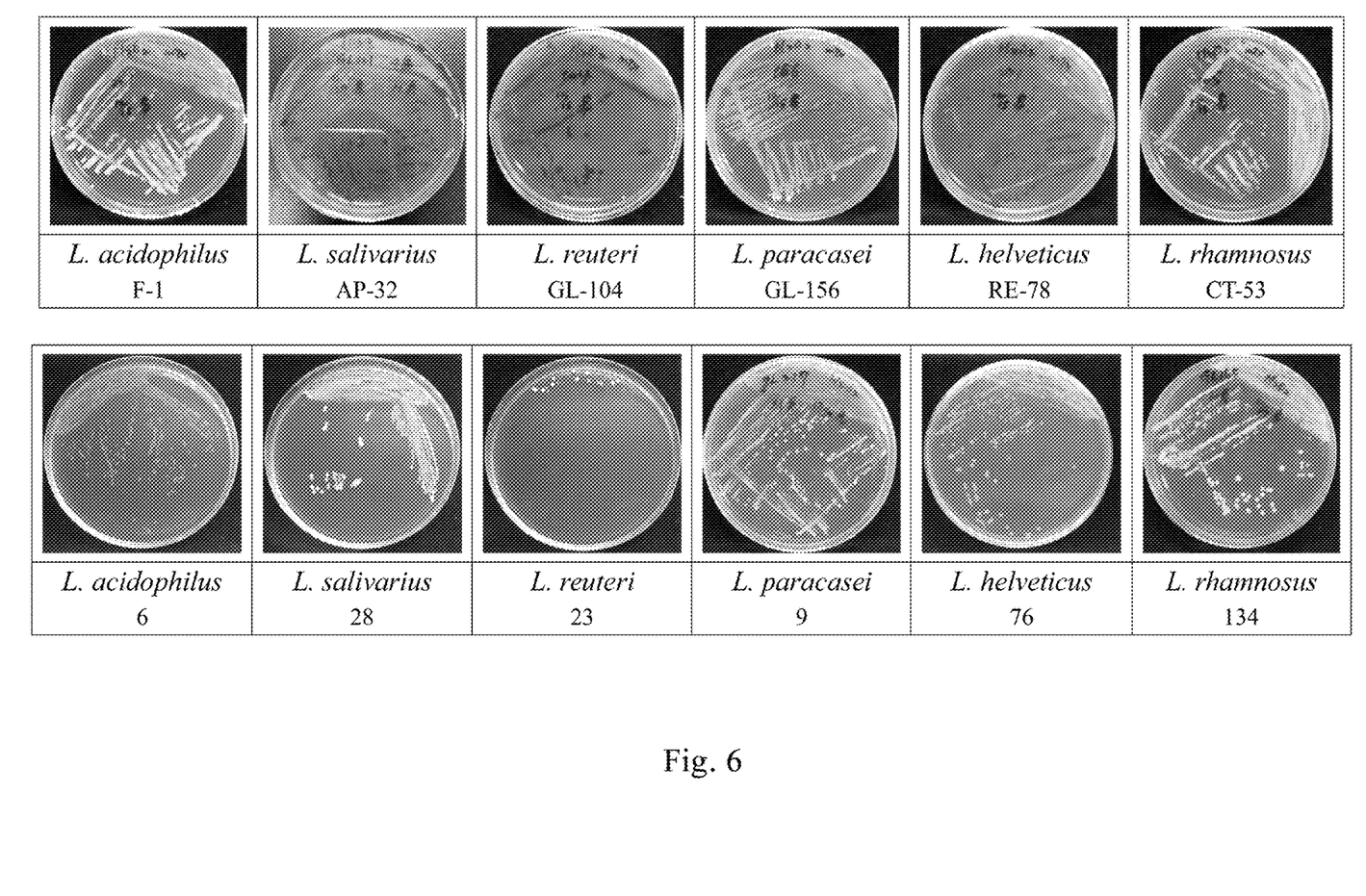
FIG. 6 shows the experimental results of secreting hydrogen peroxide on culture plates by the *Lactobacillus* strains of the present invention.
Figure 7:
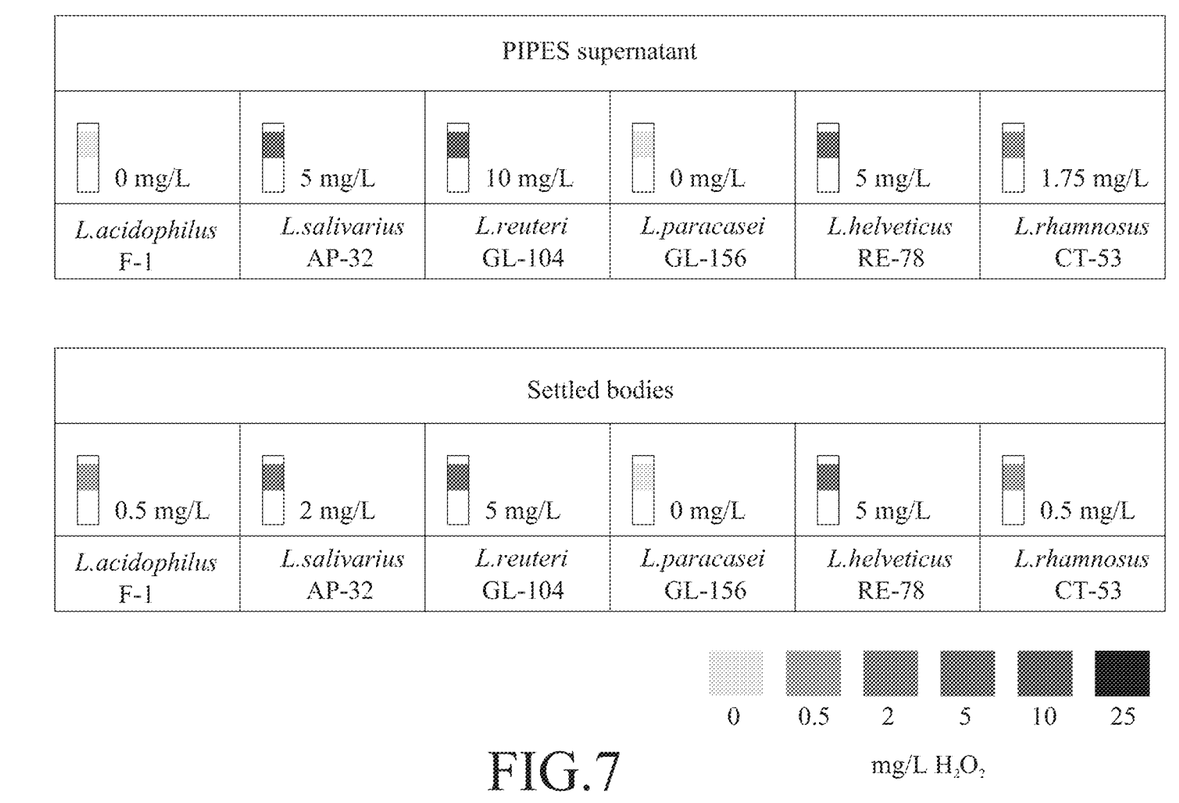
FIG. 7 shows the experimental results of using test papers to detect hydrogen peroxide secreted by the *Lactobacillus* strains of the present invention.

The experimental results are shown in FIG. 6 and FIG. 7. FIG. 6 shows the abilities of secreting hydrogen peroxide of *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus helveticus* RE-78 strain, and *Lactobacillus rhamnosus* CT-53 strain after they are cultivated on the hydrogen peroxide detection plates. FIG. 7 shows the hydrogen peroxide concentrations presented by the hydrogen peroxide test papers where are dripped the bodies or metabolites of *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus helveticus* RE-78 strain, and *Lactobacillus rhamnosus* CT-53 strain.

It is known from the experimental results shown in FIG. 6: after two-day cultivation, *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus helveticus* RE-78 strain, and *Lactobacillus rhamnosus* CT-53 strain of the present invention can all secrete hydrogen peroxide in the growth process. Different *Lactobacillus* strains of the same species, which the present invention does not claims, do not have the ability of secreting hydrogen peroxide, such as *Lactobacillus acidophilus* 6 strain, *Lactobacillus salivarius* subsp. *salicinius* 28 strain, *Lactobacillus reuteri* 23 strain, *Lactobacillus paracasei* 9 strain, *Lactobacillus helveticus* 76 strain, *Lactobacillus rhamnosus* 134 strain.

It is known from the experimental results shown in FIG. 7: among *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus helveticus* RE-78 strain and *Lactobacillus rhamnosus* CT-53 strain, *Lactobacillus salivarius* subsp. *salicinius* AP-32 strain, *Lactobacillus reuteri* GL-104 strain, *Lactobacillus helveticus* RE-78 strain and *Lactobacillus rhamnosus* CT-53 strain can diffuse the secreted hydrogen peroxide to liquid; *Lactobacillus acidophilus* F-1 strain, *Lactobacillus salivarius* subsp. *salicinius* AP-32 strain, *Lactobacillus reuteri* GL-104 strain, *Lactobacillus helveticus* RE-78 strain and *Lactobacillus rhamnosus* CT-53 strain can preserve hydrogen peroxide inside their bodies, whereby the *Lactobacillus* bodies themselves carry hydrogen peroxide. Hydrogen peroxide is not detected in *Lactobacillus paracasei* GL-156 strain matter whether in the supernatant liquid or the *Lactobacillus* bodies. This fact indicates that the metabolism generating hydrogen peroxide is slower in *Lactobacillus paracasei* GL-156 strain and that *Lactobacillus paracasei* GL-156 strain needs longer time to generate hydrogen peroxide (the metabolism is undertaken only for 5 hours in this embodiment). A trace amount of hydrogen peroxide is detected in the bodies of *Lactobacillus acidophilus* F-1 strain, but none of hydrogen peroxide is detected in the supernatant liquid of *Lactobacillus acidophilus* F-1 strain. This fact indicates that *Lactobacillus acidophilus* F-1 strain is just starting to secrete hydrogen peroxide after five-hour metabolism. Therefore, *Lactobacillus acidophilus* F-1 strain is also a strain needing longer time to generate sufficient hydrogen peroxide.

Embodiment III: oral pathogen-inhibiting ability of lactobacilli able to maintain oral health Whether lactobacilli can protect oral health is dependent on whether their ability to resist oral pathogens is strong sufficiently. Oral pathogens not only include well-known *Streptococcus mutans* but also include *Fusobacterium nucleatum* subsp. *polymorphum, Aggregatibacter actinomycetemcomitans*, and *Porphyromonas gingivalis*. *Streptococcus mutans* causes caries; *Fusobacterium nucleatum* subsp. *polymorphum* causes periodontitis, oral odor, colon cancer, etc.; *Aggregatibacter actinomycetemcomitans* is the main bacterium causing periodontitis, stomatitis, and pneumonia; *Porphyromonas gingivalis* is the main factor causing adult periodontitis and oral odor. Besides, *Fusobacterium nucleatum* subsp. *polymorphum, Aggregatibacter actinomycetemcomitans*, and *Porphyromonas gingivalis* all generate sulfides. Therefore, *Fusobacterium nucleatum* subsp. *Polymorphum* and *Aggregatibacter actinomycetemcomitans* are also the species affecting oral odor in addition to *Porphyromonas gingivalis*.

Hence, the Inventors undertake experiments to evaluate the pathogen-inhibiting abilities and oral health protection effects of *Lactobacillus acidophilus* F-1 strain, *Lactobacillus salivarius* subsp. *salicinius* AP-32 strain, *Lactobacillus* reuteri GL-104 strain, *Lactobacillus paracasei* GL-156 strain, *Lactobacillus helveticus* RE-78 strain, *Lactobacillus rhamnosus* CT-53 strain, and *Lactobacillus paracasei* ET-66 strain. The steps of experiments are as follows:

1. activate oral pathogens;
2. adjust the number of lactobacilli via a thermal death process, and co-cultivate lactobacilli (billion lactobacilli/ml) with oral pathogens;
3. co-cultivate lactobacilli and oral pathogens in an anaerobic environment at a temperature of 37° C. for 2-4 days;
4. count the oral pathogens.

Figure 1:
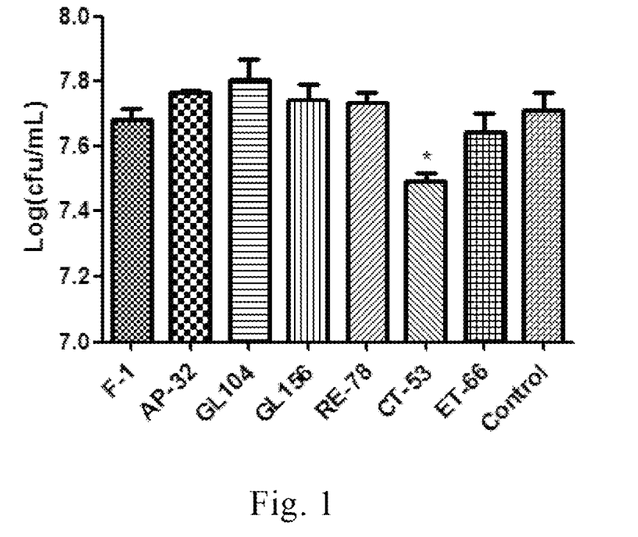
FIG. 1 shows the experimental results of the *Streptococcus mutans* inhibition effects of the *Lactobacillus* strains of the present invention.
Figure 2:
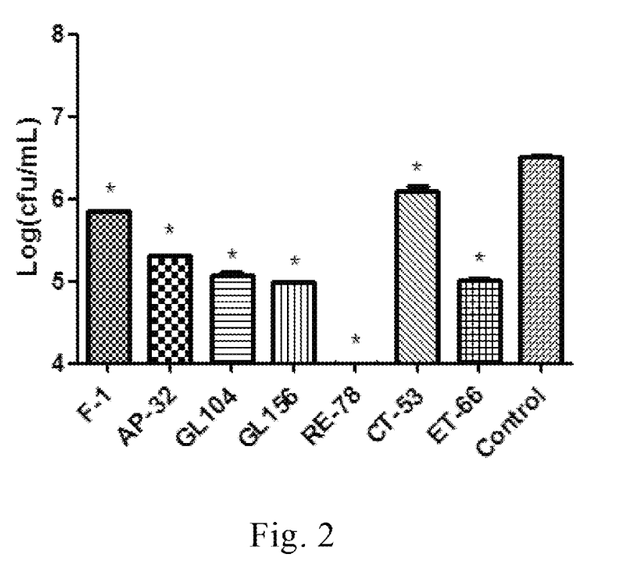
FIG. 2 shows the experimental results of the *Fusobacterium nucleatum* subsp. *polymorphum* inhibition effects of the *Lactobacillus* strains of the present invention.
Figure 3:
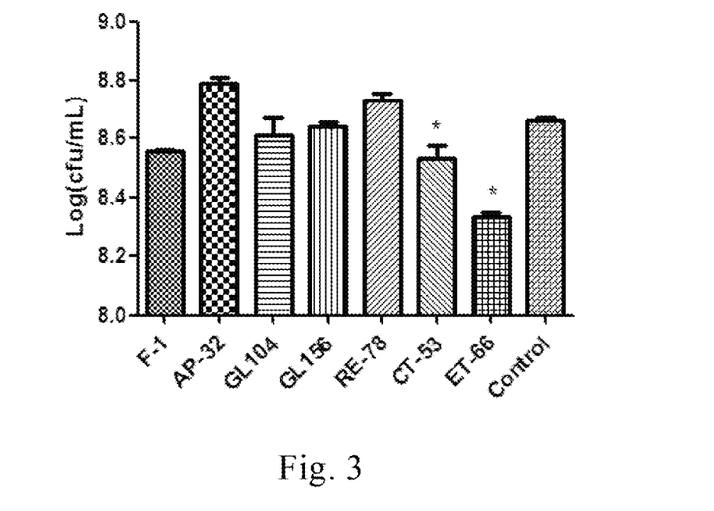
FIG. 3 shows the experimental results of the *Aggregatibacter actinomycetemcomitans* inhibition effects of the *Lactobacillus* strains of the present invention.
Figure 4:
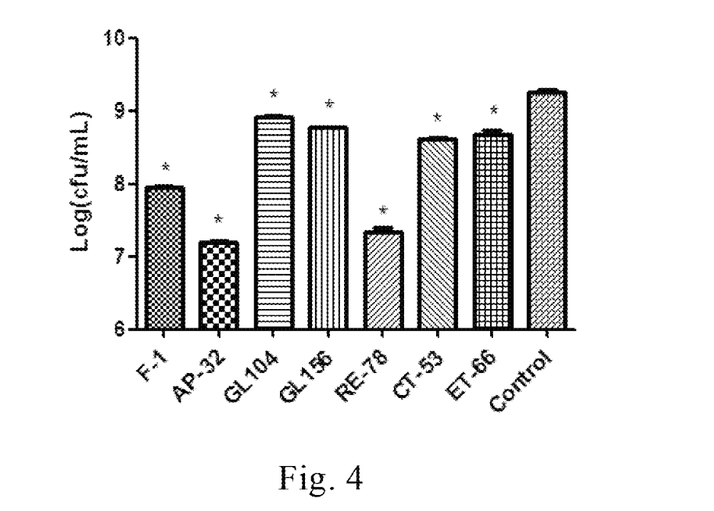
FIG. 4 shows the experimental results of the *Porphyromonas gingivalis* 17 inhibition effects of the *Lactobacillus* strains of the present invention.
Figure 5:
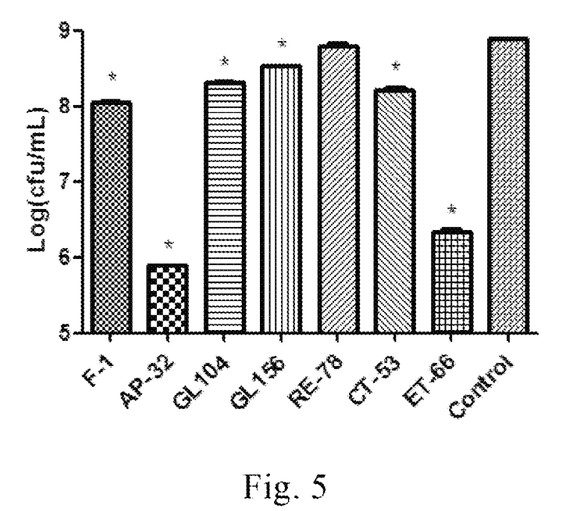
FIG. 5 shows the experimental results of the *Porphyromonas gingivalis* 18 inhibition effects of the *Lactobacillus* strains of the present invention.

The statistics of experimental data are shown in Table.3 and FIGS. 1-5. FIG. 1 is a diagram showing the analysis of the *Streptococcus mutans* inhibiting abilities of the lactobacilli of the present invention. FIG. 2 is a diagram showing the analysis of the *Fusobacterium nucleatum* subsp. *polymorphum* inhibiting abilities of the lactobacilli of the present invention. FIG. 3 is a diagram showing the analysis of the *Aggregatibacter actinomycetemcomitans* inhibiting abilities of the lactobacilli of the present invention. FIG. 4 and FIG. 5 are diagrams showing the analysis of the *Porphyromonas gingivalis* inhibiting abilities of the lactobacilli of the present invention. All the data are expressed in form of Mean±SD and compared with the control group.

FIG. 1 shows the survival rate of *Streptococcus mutans* co-cultivated with *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus helveticus* RE-78 strain, *Lactobacillus rhamnosus* CT-53 strain, and *Lactobacillus paracasei* ET-66 strain. As shwin in FIG. 1, *Lactobacillus rhamnosus* CT-53 strain of the present invention has the most significant *Streptococcus mutans* inhibiting effect.

FIG. 2 shows the survival rate of *Fusobacterium nucleatum* subsp. *polymorphum* co-cultivated with *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus helveticus* RE-78 strain, *Lactobacillus rhamnosus* CT-53 strain, and *Lactobacillus paracasei* ET-66 strain. As shwin in FIG. 2, *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus helveticus* RE-78 strain, *Lactobacillus rhamnosus* CT-53 strain, and *Lactobacillus paracasei* ET-66 strain of the present invention all have obvious *Fusobacterium nucleatum* subsp. *polymorphum* inhibiting effect.

FIG. 3 shows the survival rate of *Aggregatibacter actinomycetemcomitans* co-cultivated with *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus helveticus* RE-78 strain, *Lactobacillus rhamnosus* CT-53 strain, and *Lactobacillus paracasei* ET-66 strain. As shwin in FIG. 3, *Lactobacillus rhamnosus* CT-53 strain and *Lactobacillus paracasei* ET-66 strain of the present invention have more significant *Aggregatibacter actinomycetemcomitans* inhibiting effect.

FIG. 4 shows the survival rate of *Porphyromonas gingivalis* 17 co-cultivated with *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus helveticus* RE-78 strain, *Lactobacillus rhamnosus* CT-53 strain, and *Lactobacillus paracasei* ET-66 strain. As shwin in FIG. 4, *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus helveticus* RE-78 strain, *Lactobacillus rhamnosus* CT-53 strain, and *Lactobacillus paracasei* ET-66 strain of the present invention all have obvious *Porphyromonas gingivalis* 17 inhibiting effect.

FIG. 5 shows the survival rate of *Porphyromonas gingivalis* 18 co-cultivated with *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus helveticus* RE-78 strain, *Lactobacillus rhamnosus* CT-53 strain, and *Lactobacillus paracasei* ET-66 strain. As shwin in FIG. 5, except *Lactobacillus helveticus* RE-78 strain, *Lactobacillus acidophilus* F-1 strain, *Lactobacillus salivarius* subsp. *salicinius* AP-32 strain, *Lactobacillus reuteri* GL-104 strain, *Lactobacillus paracasei* GL-156 strain, *Lactobacillus rhamnosus* CT-53 strain, and *Lactobacillus paracasei* ET-66 strain of the present invention all have obvious *Porphyromonas gingivalis* 17 inhibiting effect.

Table.3 shows the oral pathogen inhibition rate of the *Lactobacillus* strains of the present invention. The strains of the present invention that can inhibit all five strains of pathogens include *Lactobacillus acidophilus* F-1 strain, *Lactobacillus rhamnosus* CT-53 strain, and *Lactobacillus paracasei* ET-66 strain. *Lactobacillus rhamnosus* CT-53 strain has the best *Streptococcus mutans* inhibiting effect. *Lactobacillus reuteri* GL-104 strain and *Lactobacillus paracasei* GL-156 strain can inhibit four strains of oral pathogens, but they fail to inhibit *Streptococcus mutans*. *Lactobacillus salivarius* subsp. *salicinius* AP-32 strain and *Lactobacillus helveticus* RE-78 strain can inhibit three strains of the oral pathogens, but they fail to inhibit *Streptococcus mutans* and *Aggregatibacter actinomycetemcomitans*. *Lactobacillus salivarius* subsp. *salicinius* AP-32 strain can inhibit three strains of the oral pathogens to an inhibition rate of as high as over 90%, and the three strains of the oral pathogens all closely correlate with oral odor. Therefore, *Lactobacillus salivarius* subsp. *salicinius* AP-32 strain has high potential of applying to oral cleaning and refreshing products.

TABLE 3 oral pathogen inhibition rates of seven *lactobacillus* strains

| Strain | Oral pathogen inhibition rate (%) | | | | |
| --- | --- | --- | --- | --- | --- |
| | *Streptococcus mutans* | *Fusobacterium nucleatum* subsp. *polymorphum* | *Aggregatibacter actinomycetemcomitans* | *Porphyromonas gingivalis* | *Porphyromonas gingivalis* |
| *Lactobacillus acidophilus* F-1 strain | 6.81 ± 8.95 | 78.53 ± 1.05 | 21.35 ± 0.88 | 94.83 ± 0.96 | 85.14 ± 0.79 |

TABLE 3-continued oral pathogen inhibition rates of seven *lactobacillus* strains

| Strain | Oral pathogen inhibition rate (%) | | | | |
|---|---|---|---|---|---|
| | *Streptococcus mutans* | *Fusobacterium nucleatum* subsp. *polymorphum* | *Aggregatibacter actinomycetemcomitans* | *Porphyromonas gingivalis* | *Porphyromonas gingivalis* |
| *Lactobacillus salivarius* subsp. *salicinius* AP-32 strain | −16.07 ± 26.03 | 93.77 ± 0.23 | −34.96 ± 5.57 | 99.1 ± 0.18 | 99.9 ± 0.01 |
| *Lactobacillus reuteri* GL-104 strain | −25.02 ± 12.13 | 96.31 ± 0.42 | 9.5 ± 16.65 | 53.56 ± 5.93 | 73.36 ± 1.21 |
| *Lactobacillus paracasei* GL-156 strain | −8.8 ± 19.77 | 96.93 ± 0.19 | 4.05 ± 0.49 | 66.90 ± 5.99 | 56.44 ± 1.91 |
| *Lactobacillus helveticus* RE-78 strain | −6.38 ± 11.05 | 100.00 ± 0.00 | −17.05 ± 6.73 | 98.77 ± 0.18 | 19.57 ± 7.94 |
| *Lactobacillus rhamnosus* CT-53 | 38.83 ± 10.25 | 60.85 ± 6.08 | 25.16 ± 11.06 | 77.37 ± 3.21 | 78.78 ± 3.1 |
| *Lactobacillus paracasei* ET-66 strain | 14.18 ± 2.25 | 96.84 ± 0.05 | 52.92 ± 1.15 | 73.64 ± 2.62 | 99.72 ± 0.02 |

In conclusion, the present invention discloses side effect-free and health-enhancing *Lactobacillus* strains to provide a new option for keeping oral health. The *Lactobacillus* strain-containing food composite and medical composite of the present invention can inhibit the growth of oral pathogens, applicable to caries prevention, periodontitis prevention, and oral odor elimination. The hydrogen peroxide-secreting *Lactobacillus* strains of the present invention can apply to teeth whitening.

The embodiments described above are to demonstrate the technical thoughts and characteristics of the present invention to enable the persons skilled in the art to understand, make, use the present invention. However, these embodiments are only to exemplify the present invention but not to limit the scope of the present invention. Any equivalent modification or variation according to the spirit of the present invention is to be also included by the scope of the present invention.

Biological Material Preservation

[1] China Center for Type Culture Collection, Apr. 10, 2011, CCTCC NO: M2011124;
[2] China Center for Type Culture Collection, Apr. 10, 2011, CCTCC NO: M2011127;
[3] China Center for Type Culture Collection, Aug. 7, 2009, CCTCC NO: M209138;
[4] China Center for Type Culture Collection, Nov. 24, 2014, CCTCC NO: M2014590
[5] China General Microbiological Culture Collection Center, Dec. 29, 2016, CGMCC No. 13513;
[6] China Center for Type Culture Collection, Apr. 10, 2011, CCTCC NO: M2011129;
[7] China General Microbiological Culture Collection Center, Dec. 29, 2016, CGMCC No. 13514.

What is claimed is:

1. A method of inhibiting oral pathogens comprising administering to a human subject in need thereof a composite comprising:

an isolated *Lactobacillus paracasei* ET-66 strain, CGMCC No. 13514; and
an excipient, diluent, or carrier, which is physiologically or medically acceptable,
wherein a number of the isolated *Lactobacillus paracasei* ET-66 strain, CGMCC No. 13514 is over $10^6$ CFU.

2. The method according to claim 1, wherein the *Lactobacillus* strain is an active strain.

3. The method according to claim 1, wherein the composite further includes a *Lactobacillus* strain selected from the group consisting of *Lactobacillus acidophilus* F-1 strain, CCTCC NO: M2011124; *Lactobacillus salivarius* subsp. *salicinius* AP-32 strain, CCTCC NO: M2011127; *Lactobacillus reuteri* GL-104 strain, CCTCC NO: M209138; *Lactobacillus rhamnosus* CT-53 strain, CCTCC NO: M2011129; and combinations thereof.

4. The method according to claim 3, wherein the *Lactobacillus* strain is a deactivated strain.

5. The method according to claim 1, wherein the isolated *Lactobacillus paracasei* ET-66 strain is a deactivated strain.

6. The method according to claim 1, wherein the oral pathogens include *Streptococcus mutans*, *Fusobacterium nucleatum* subsp. *polymorphum*, *Aggregatibacter actinomycetemcomitans*, and *Porphyromonas gingivalis*.

7. The method according to claim 1, wherein the composite is a food composite, medical composite, or oral cleaning composite.

8. The method according to claim 7, wherein the medical composite is in an oral form or a topical form.

9. The method according to claim 1, wherein the excipient or diluent is a food.

10. The method according to claim 9, wherein the food is selected from a milk-based drink, tea, coffee, a chewing gum, a tooth-cleaning candy, and combinations thereof.

11. The method according to claim 1, wherein the composite is an oral cleaning product selected from a toothpaste, a dental powder, a mouthwash, a fresh-breath spray, a fluorine-coating agent, and a false tooth cleaning agent.

12. The method according to claim 1, wherein the carrier is a toothbrush, an interdental brush, a dental floss, or an oral cotton stick.

13. The method according to claim 1, wherein the composite further includes another *Lactobacillus* strain selected from the group consisting of *Lactobacillus paracasei* GL-156 strain, CCTCC No: M2014590; *Lactobacillus helveticus* RE-78 strain, CGMCC No. 13513; and a combination thereof.

14. The method according to claim 13, wherein the another *Lactobacillus* strain is a deactivated strain.

\* \* \* \* \*